United States Patent
Jantharasuk et al.

(10) Patent No.: US 11,286,218 B2
(45) Date of Patent: Mar. 29, 2022

(54) HYDROCARBON CONVERSION PROCESS

(71) Applicant: SMH Co., Ltd, Bangkok (TH)

(72) Inventors: Amnart Jantharasuk, Rayong (TH); Kongkiat Suriye, Samut-Prakan (TH)

(73) Assignee: SMH Co., Ltd, Bangkok (TH)

( * ) Notice: Subject to any disclaimer, the term of this patent is extended or adjusted under 35 U.S.C. 154(b) by 0 days.

(21) Appl. No.: 16/468,796

(22) PCT Filed: Nov. 16, 2017

(86) PCT No.: PCT/EP2017/079495
§ 371 (c)(1),
(2) Date: Jun. 12, 2019

(87) PCT Pub. No.: WO2018/108442
PCT Pub. Date: Jun. 21, 2018

(65) Prior Publication Data
US 2019/0359543 A1    Nov. 28, 2019

(30) Foreign Application Priority Data
Dec. 13, 2016 (EP) .................................. 16203696

(51) Int. Cl.
| | | |
|---|---|---|
| C07C 5/333 | (2006.01) |
| B01J 21/08 | (2006.01) |
| B01J 23/63 | (2006.01) |
| B01J 29/16 | (2006.01) |
| B01J 35/00 | (2006.01) |
| B01J 37/02 | (2006.01) |
| B01J 37/04 | (2006.01) |
| B01J 37/08 | (2006.01) |
| B01J 38/12 | (2006.01) |
| C10G 11/05 | (2006.01) |

(52) U.S. Cl.
CPC ............. *C07C 5/3337* (2013.01); *B01J 21/08* (2013.01); *B01J 23/63* (2013.01); *B01J 29/166* (2013.01); *B01J 35/0006* (2013.01); *B01J 37/0205* (2013.01); *B01J 37/0236* (2013.01); *B01J 37/04* (2013.01); *B01J 37/088* (2013.01); *B01J 38/12* (2013.01); *C10G 11/05* (2013.01); *C07C 2521/04* (2013.01); *C07C 2521/08* (2013.01); *C07C 2521/10* (2013.01); *C07C 2523/10* (2013.01); *C07C 2523/30* (2013.01); *C07C 2529/16* (2013.01); *C10G 2300/70* (2013.01); *C10G 2400/20* (2013.01)

(58) Field of Classification Search
CPC ........ C07C 5/333; C07C 5/3337; C07C 5/321
See application file for complete search history.

(56) References Cited

U.S. PATENT DOCUMENTS

| | | | |
|---|---|---|---|
| 3,932,548 A | | 1/1976 | Rausch |
| 3,980,721 A | * | 9/1976 | Juguin ..................... B01J 23/64 585/430 |
| 5,453,558 A | * | 9/1995 | Alexander ............... B01J 29/62 208/138 |

FOREIGN PATENT DOCUMENTS

| | | | | |
|---|---|---|---|---|
| EP | 2689843 A1 | * | 1/2014 | .......... B01J 37/0215 |
| EP | 2689843 A1 | | 1/2014 | |
| EP | 3050621 A1 | | 8/2016 | |
| WO | WO-2014163590 A1 | * | 10/2014 | .......... C07C 5/3335 |
| WO | WO-2016005896 A2 | * | 1/2016 | .......... B01J 35/002 |

OTHER PUBLICATIONS

Jesper et al. (Catalytic dehydrogenation of light alkanes on metals and metal oxides, 2014, Chemical Reviews, 114, 10613-10653) (Year: 2014).*
Jan. 31, 2018, International Search Report and Written Opinion, PCT/EP2017/079495.

* cited by examiner

*Primary Examiner* — Youngsul Jeong
(74) *Attorney, Agent, or Firm* — Banner & Witcoff, Ltd.

(57) ABSTRACT

The present invention relates to a hydrocarbon conversion process comprising contacting a hydrocarbon feed stream with a hydrocarbon conversion catalyst, wherein the hydrocarbon conversion catalyst comprises a first composition comprising a dehydrogenation active metal on a solid support; and a second composition comprising a transition metal and a doping agent on an inorganic support, wherein the doping agent is selected from zinc, gallium, indium, lanthanum, and mixtures thereof.

19 Claims, No Drawings

HYDROCARBON CONVERSION PROCESS

CROSS-REFERENCE TO RELATED APPLICATIONS

This application is a U.S. National Stage application under 35 U.S.C. § 371 of International Application PCT/EP2017/079495 (published as WO 2018/108442 A1), filed Nov. 16, 2017, which claims the benefit of priority to Application EP 16203696.6, filed Dec. 13, 2016. Benefit of the filing date of each of these prior applications is hereby claimed. Each of these prior applications is hereby incorporated by reference in its entirety.

The present invention relates to a process for conversion of a hydrocarbon feed comprising a saturated hydrocarbon compound to olefin products.

Olefins, especially light olefins including ethylene and propylene, are valuable hydrocarbon products. They are useful for preparing a wide variety of end products, including ethylene oxide, propylene oxide, ethyl benzene, acetone, phenol, polyethylene, polypropylene, other polymers, and other petrochemical products. Even though the prices have fluctuated over time, the demands in the industry have still been continuously wing.

To serve industrial needs, many methods have been used to produce olefins. However, it is typically more economically attractive to produce olefins from lower valued feedstock such as paraffins. A conventional method for converting saturated paraffins to olefins is thermal cracking. This is a highly energy intensive method and product selectivity is difficult to be adjusted and controlled.

Catalytic cracking is a later developed method. With appropriate catalytic materials, generally zeolite-based materials, hydrocarbon cracking can occur at less severe operating conditions.

In the art, also processes are known converting saturated paraffins to olefins by dehydrogenation utilizing an appropriate catalyst. The dehydrogenation may be followed by an appropriate metathesis step, in order to finally provide an olefin distribution which fulfills highest industrial needs.

Diverse side reactions may take place during dehydrogenation and metathesis, for example the (re)hydrogenation of ethylene, propylene or butene which are otherwise preferred end products of a dehydrogenation reaction of ethane, propane or butane. Further, in the presence of hydrogen, hydrogenolysis and cracking of feed materials, such as propane, may occur. Thus, the development of hydrogen may be a drawback in further reacting obtained olefins.

It is therefore an object of the present invention to provide a hydrocarbon conversion process wherein side reactions of hydrogen may be decreased or substantially prevented.

This object is achieved by a hydrocarbon conversion process comprising contacting a hydrocarbon feed stream with a hydrocarbon conversion catalyst, wherein the hydrocarbon conversion catalyst comprises:

a first composition comprising a dehydrogenation active metal on a solid support; and a second composition comprising a transition metal and a doping agent on an inorganic support, wherein the doping agent is selected from zinc, gallium, indium, lanthanum, and mixtures thereof.

In the hydrocarbon conversion catalyst, it may be provided that the first composition is different from the second composition. Likewise, the solid support comprised in the first composition may be different from the inorganic support comprised in the second composition. Similarly, the dehydrogenation active metal comprised in the first composition is preferably different from the transition metal comprised in the second composition.

In another embodiment, it may be provided that the second composition does not comprise the dehydrogenation active metal, in particular the second composition does not comprise platinum, palladium, rhodium, chromium or mixtures thereof.

In a further embodiment, the inorganic support comprised in the second composition comprises $SiO_2$, HY-zeolite or mixtures thereof and the solid support comprised in the first composition comprises a mixture of silica and zirconia.

In a further embodiment, the solid support comprised in the first composition may be a mixed magnesium-aluminium oxide and the inorganic support comprised in the second composition is a mixture of Y-zeolite, and $SiO_2$, preferably with an amount of Y-zeolite from 1 to 8 wt.-%, and balancing $SiO_2$.

The dehydrogenation active metal refers to a group of metals that are efficient for dehydrogenation of a hydrocarbon. Dehydrogenation is a reaction in which hydrogen is detached from a molecule. In one embodiment, the dehydrogenation active metal is selected from platinum, palladium, iridium, chromium, and mixtures thereof, preferably platinum.

In one embodiment, the solid support is selected from aluminium oxide, silicon dioxide, zirconium dioxide, titanium dioxide, magnesium oxide, calcium oxide, and mixtures thereof.

In another embodiment, the solid support comprises a mixed magnesium-aluminium oxide and/or a calcium-aluminium oxide.

Additional active metal, which acts to enhance catalytic activity of this first composition, such as potassium, tin, lanthanum, indium, yttrium, ytterbium, rhenium, and mixtures thereof, may be also present in the first composition, preferably tin, indium, and a mixture thereof.

In one embodiment, the first composition contains 0.01 to 25 wt % of the dehydrogenation active metal, preferably 0.05 to 20 wt % of the dehydrogenation active metal, more preferably 0.1 to 5 wt % of the dehydrogenation active metal, based on the total weight of the first composition.

In one embodiment, platinum is the dehydrogenation active metal, $Al_2O_3$ is the solid support and tin and/or potassium are additional active metals in the first composition.

In another embodiment, platinum is the dehydrogenation active metal, $SiO_2$ and $ZrO_2$ are the solid support and yttrium and/or ytterbium are additional active metals in the first composition.

In a further embodiment, platinum is the dehydrogenation active metal, a mixed magnesium-aluminium oxide and/or a mixed calcium-aluminium oxide is the solid support, and indium and/or tin is the additional active metal in the first composition.

In one embodiment, the mixed magnesium-aluminium oxide and the mixed calcium-aluminium oxide in the first composition are derived from a magnesium-aluminium or calcium-aluminium layered double hydroxide, which can be preferably obtained by subjecting a magnesium-aluminium or calcium-aluminium layered double hydroxide to a temperature in the range of 600-700° C., more preferably 600-650° C., for more 2 hours, more preferably 3 to 10 hours.

Preferably, the first composition contains 0.005 to 2 wt % of the additional active metal based on the total weight of the first composition.

Preferably, the combined amount of the dehydrogenation active metal, the solid support, and the additional active metal present in the first composition is at least 90%, more preferably at least 95%, by weight of the first composition. In a particular embodiment, the first composition consists of the dehydrogenation active metal, the solid support, and optionally the additional active metal. In one embodiment, the transition metal of the second composition is selected from molybdenum, tungsten, rhenium, and mixtures thereof.

The transition metal is preferably tungsten, more preferably in the form of tungsten oxide.

In one embodiment, the inorganic support is selected from aluminium oxide, silicon dioxide, zircon dioxide, titanium dioxide, zeolite, and mixtures thereof, preferably silicon dioxide or a mixture of silicon dioxide and zeolite.

In one embodiment, the second composition comprises tungsten, and a doping agent selected from zinc, gallium, indium, lanthanum, and mixtures thereof on an inorganic support comprising a of silicon dioxide and zeolite.

Preferably, the zeolite is selected from ZSM-5, X-zeolite, Y-zeolite, beta-zeolite, MCM-22, ferrierite, and mixtures thereof, more preferably Y-zeolite.

In another preferred embodiment, the second composition further comprises a mixed metal oxide, more preferably a mixed magnesium-aluminium oxide or a mixed calcium-aluminium oxide, wherein the mixed metal oxide is preferably physically mixed with the transition metal and the doping agent on the inorganic support.

In a particularly preferred embodiment, the second composition contains tungsten oxide and a doping agent selected from zinc, gallium, indium, lanthanum, and mixtures thereof on an inorganic support comprising a mixture of silicon dioxide and Y-zeolite physically mixed with a mixed magnesium-aluminium oxide.

Even more preferably is the mixed magnesium-aluminium oxide derived from a magnesium-aluminium layered double hydroxide precursor.

In one embodiment, the second composition contains 1 to 15 wt % of the transition metal, even more preferably 5 to 10 wt % of the transition metal, based on the total weight of the second composition.

In the second composition, the doping agent is present in one embodiment in amount of 0.1-10 wt %, in one embodiment in an amount of 1-5 wt %, based on the total weight of the second composition.

Preferably, the combined amount of the transition metal, the inorganic support, the mixed metal oxide, and the optional doping agent present in the second composition is at least 90%, more preferably at least 95%, by weight of the second composition. In a particular embodiment, the second composition consists of the transition metal, the inorganic support, the mixed metal oxide, and the doping agent. In one embodiment the dehydrogenation active metal is platinum, the transition metal is tungsten and the doping agent is indium.

The first composition is preferably prepared by supporting all element precursors of the dehydrogenation active metal and the optional additional active metal on the solid support followed by a suitable heat treatment.

Similarly, the second composition is preferably prepared by supporting on the inorganic support all element precursors of the transition metal the doping agent followed by a suitable heat treatment.

Element precursors are starting compounds containing the desired elements which can be converted to the desired form of the elements in the final hydrocarbon conversion catalyst by the suitable heat treatment. For example, the element precursors may include oxides, halides.

More preferably, the first composition is prepared by impregnating, preferably simultaneously (co-impregnation), the element precursors of the dehydrogenation active metal and the optional addition active metal, which are provided in solution form, on the solid support followed by calcination. The calcination is preferably carried out in oxidizing atmosphere, at a temperature in the range of 300-800° C. for 1-24 hours, even more preferably 400-600° C. for 2-10 hours.

Also more preferably, the second composition is prepared by impregnating, preferably sequentially, the element precursors of the transition metal and the doping agent, which are provided in solution form, on the inorganic support followed by calcination. The calcination is preferably carried out in oxidizing atmosphere, at a temperature in the range of 300-800° C. for 1-24 hours, even more preferably 400-600° C. for 2-10 hours. Further preferred is the precursor of the doping agent is impregnated on the inorganic support prior to the precursor of the transition metal.

The obtained first and second compositions from the preparation method described above generally in the powder form with average size lower than 800 micrometers.

In one embodiment, the first composition and the second composition are physically mixed, preferably in a weight ratio of the first to the second composition from 1:10 to 10:1, more preferably 1:5 to 5:1, even more preferably 1:3 to 3:1, and even further preferably 1:2 to 2:1, to form the hydrocarbon conversion catalyst.

The hydrocarbon conversion catalyst can be in a powder form in one embodiment. In another embodiment, the hydrocarbon conversion catalyst can be also formed into a shape that is more suitable for industrial utilization, for example, pellet, tablet, extrudate, or sphere.

Physical mixing of the first and the second compositions can be carried out before or after shaping of the hydrocarbon conversion catalyst.

In one embodiment, the first composition and the second composition are separately formed into desired shapes, then the first composition formed into the desired shape and the second composition formed into the desired shape are physically mixed to obtain the hydrocarbon conversion catalyst.

In a more preferred embodiment, powder of the first composition and powder of the second composition are physically mixed to obtain the hydrocarbon conversion catalyst, and the obtained hydrocarbon conversion catalyst may then be formed into any desired shape.

In shaping of the first composition, the second composition, or the hydrocarbon conversion catalyst, a binding material can be added to facilitate formation of powder into the desired shape. Any binding material known in the art may be used.

In another embodiment, it is also possible that the first and the second compositions are provided in macroscopic scale layer form, wherein the first composition and the second composition are arranged as separate layers in a fixed-bed reactor.

According to the invention, in one embodiment, the hydrocarbon feed stream comprises at least one paraffin having 2 to 5 carbon atoms, preferably selected from propane, n-butane, and mixtures thereof. In another embodiment, the hydrocarbon feed stream comprises a paraffin selected from ethane, propane, butane, pentane and mixtures thereof, preferably propane.

The hydrocarbon conversion process can be operated in a wide range of operating conditions. However, some specific ranges of operating conditions can result in high olefins productions selectivity.

In an embodiment, the process is carried out at a temperature in the range of 200-800° C., preferably 350-700° C., even more preferably 450-650° C.

In another embodiment, the process is carried out at a pressure in the range of 0.01 to 10 bar gauge, preferably 0.05 to 5 bar gauge.

The contact time needed to obtain a desirable yield of olefins products depends upon several factors, such as operating temperature, operating pressure, and catalyst activity. In one embodiment, the process is carried out at a weight hourly space velocity (WHSV) in the range of 0.01 to $20^{-1}$, preferably 0.05 to $5^{-1}$.

The process can be conducted in a batch manner or continuous manner. For commercial scale, it is favorable that the process is continuously operated. Continuous operation can be performed with fixed bed, fluidized bed, or other techniques known in the art with fixed bed being typically preferred.

Prior to contacting with the hydrocarbon feed stream, the hydrocarbon conversion catalyst is preferably pretreated. The pretreatment condition may include contacting the catalyst system with an inert gas, an oxidizing gas, a reducing gas, or mixtures thereof, at an elevated temperature, preferably 250° C. to 850° C., more preferably 400° C. to 750° C., even more preferably 500° C. to 700° C. In one preferred embodiment, the pretreatment condition includes contacting the catalyst with a reducing gas, more preferably hydrogen, at a temperature in the range of 400-600° C. for approximately 0.5 to 8 hours.

After contact with the hydrocarbon feed stream at the operating conditions, some poisonous substances, heavy hydrocarbons, and coke may deposit on the surface of the hydrocarbon conversion catalyst. This normally affects activity of the catalyst to gradually drop over A suitable regeneration can be performed on the used hydrocarbon conversion catalyst to recover at least some of its activity.

In an embodiment, the hydrocarbon conversion process further comprises a regeneration step wherein the regeneration step includes contacting the hydrocarbon conversion catalyst with an oxidizing agent at a high temperature. The regeneration step should be carefully controlled to avoid overheating and destroying structure of the catalyst. In an embodiment, the regeneration step is carried out by contacting the used hydrocarbon conversion catalyst with an oxidizing gas, preferably oxygen or air, at a temperature in the range of 200-700° C., preferably 300-600° C. Other known regeneration techniques can be employed without limitation.

A variety of hydrocarbon conversion process according to the invention has been set up and tested according to the above disclosure. It was surprisingly found by the inventors that the hydrocarbon conversion process according to the present invention featured increased total olefins selectivity with decreased $CH_4$ production, in comparison to non-inventive process.

Furthermore, it was surprisingly found that the hydrocarbon conversion process of the present invention can be operated under mild conditions, i.e. at temperatures significantly lower known in the art for converting paraffin to olefin.

EXPERIMENTAL RESULTS

In the examples section below, the conversion of propane into olefins, preferably ethylene and butene, has been investigated using a hydrocarbon conversion catalyst according to the present invention and a comparative catalyst.

Example 1 Comparative

A solution of chloroplatinic acid hexahydrate and a solution of ytterbium trinitrate are co-impreganted onto powder of silica-zirconia mixture, then the resulting material was dried at 100° C. for 2 hours, followed by calcination under air at 700° C. for 3 hours to obtain a first composition containing 1 wt % Pt and 0.15 wt % Yb and balancing $SiO_2$—$ZrO_2$, wherein the weight percentages based on the total weight of the first composition.

A support for a second composition was prepared by mixing $SiO_2$ with HY-Zeolite. The $SiO_2$-Zeolite support was then impregnated using a solution of ammonium metatungstate hydrate, then dried at 110° C. for 3 hours. The resulted material was then mixed with Mg—Al—CO3 layered double hydroxide followed by calcination under air at 550° C. for 2 hours to obtain a second composition containing 7 wt % W, 4 wt % Y-zeolite, 9 wt % Mg—Al oxide, and balancing SiO2, wherein the weight percentages are based on the total weight of the second composition.

The first composition and the second composition were physically mixed 1:1 by weight to obtain Example 1 catalyst.

Example 2

A first composition is prepared the s y as described in Example 1.

A support for a second composition was prepared by mixing $SiO_2$ with HY-Zeolite. The $SiO_2$-Zeolite support was then impregnated using a solution of ammonium metatungstate hydrate, then dried at 110° C. for 3 hours. The dried mixture was then impregnated using a solution of zinc nitrate hexahydrate, then left to dry once again at 110° C. for 3 hours. The resulted material was then mixed with Mg—Al—CO3 layered double hydroxide followed by calcination under air at 550° C. for 2 hours to obtain a second composition containing 7 wt % W, 4 wt % Zn, 4 wt % Y-zeolite, 9 wt % Mg—Al oxide, and balancing SiO2, wherein the weight percentages are based on the total weight of the second composition.

The first composition and the second composition were physically mixed 1:1 by weight to obtain Example 2 catalyst.

Example 3

A first composition is prepared the same way as described in Example 1.

A support for a second composition was prepared by mixing $SiO_2$ with HY-Zeolite. The $SiO_2$-Zeolite support was then impregnated using a solution of ammonium metatungstate hydrate, then dried at 110° C. for 3 hours. The dried mixture was then impregnated using a solution of indium trinitrate, then left to dry once again at 110° C. for 3 hours. The resulted material was then mixed with Mg—Al—CO3 layered double hydroxide followed by calcination under air at 550° C. for 2 hours to obtain a second composition containing 7 wt % W, 2 wt % In, 4 wt % Y-zeolite, 9 wt % Mg—Al oxide, and balancing SiO2, wherein the weight percentages are based on the total weight of the second composition.

The first composition and the second composition were physically mixed 1:1 by weight to obtain Example 3 catalyst.

Example 4

A first composition is prepared the same way as described in Example 1.

A support for a second composition was prepared by g SiO$_2$ with HY-Zeolite. The SiO$_2$-Zeolite support was then impregnated using a solution of ammonium metatungstate hydrate, then dried at 110° C. for 3 hours. The dried mixture was then impregnated using a solution of lanthanum (III) nitrate hexahydrate, then left to once again at 110° C. for 3 hours. The resulted material was then mixed with Mg—Al—CO3 layered double hydroxide followed by calcination under at 550° C. for 2 hours to obtain a second composition containing 7 wt % W, 2 wt % La, 4 wt % Y-zeolite, 9 wt % Mg—Al oxide, and balancing SiO2, wherein the weight percentages are based on the total weight of the second composition.

The first composition and the second composition were physically mixed 1:1 by weight to obtain Example 4 catalyst.

Each catalyst as prepared above was packed in a q tube micro reactor and pretreated with hydrogen at approximately 600° C. for half an hour before contacted with propane at approximately 500° C., 0.05-0.1 bar gauge, and WHSV of approximately 0.1-0.2 hr$^{-1}$. The results measured at time on stream for approximately 60 hours and 100 hours are shown in the Table 1 below.

TABLE 1

| | C3H8 Conversion (% wt) | | Result Selectivity (% wt) | | | | | | | | | |
|---|---|---|---|---|---|---|---|---|---|---|---|---|
| | | | Total Olefins | | CH4 | | C2H4 | | C3H6 | | C4H8 | |
| | 60 h | 100 h | 60 h | 100 h | 60 h | 100 h | 60 h | 100 h | 60 h | 100 h | 60 h | 100 h |
| Example 1 | 19.64 | 7.25 | 74.42 | 83.78 | 8.44 | 5.47 | 2.60 | 6.58 | 59.04 | 60.76 | 12.78 | 16.44 |
| Example 2 | 15.994 | 7.510 | 85.703 | 92.367 | 2.688 | 1.838 | 3.394 | 8.298 | 71.330 | 70.128 | 10.978 | 13.941 |
| Example 3 | 17.006 | 11.950 | 87.079 | 91.335 | 1.714 | 1.183 | 3.001 | 5.663 | 72.442 | 71.039 | 11.635 | 14.632 |
| Example 4 | 17.227 | 10.957 | 80.998 | 89.495 | 5.855 | 3.949 | 2.826 | 4.285 | 65.955 | 73.758 | 12.216 | 11.451 |

As be seen from the above table, for the inventive hydrocarbon conversion process, the total olefins selectivity is significantly increased, while methane production is decreased. The high total olefins selectivity also shows that (re)hydrogenation of olefins obtained is low.

The features disclosed in the foregoing description and the claims may, both separately and in any combination thereof, be material for realizing the invention in diverse forms thereof.

The invention claimed is:

1. A hydrocarbon conversion process comprising dehydrogenation and metathesis of a hydrocarbon feed stream, said process comprising contacting the hydrocarbon feed stream with a hydrocarbon conversion catalyst, wherein the hydrocarbon conversion catalyst comprises:
   a first composition comprising a dehydrogenation active metal on a solid support, said solid support comprising aluminum oxide, silicon dioxide, zirconium dioxide, titanium dioxide magnesium oxide, calcium oxide, or a mixture of two or more thereof; and
   a second composition comprising from 1 wt-% to 15 wt-% tungsten and a doping agent on an inorganic support, wherein the doping agent is selected from zinc, gallium, indium, lanthanum, and mixtures thereof,
   wherein the solid support of the first composition is different from the inorganic support of the second composition, and
   wherein the inorganic support of the second composition comprises silicon dioxide and further comprises a mixed magnesium-aluminum oxide or a mixed calcium-aluminum oxide.

2. The hydrocarbon conversion process according to claim 1, wherein the dehydrogenation active metal is selected from platinum, palladium, iridium, chromium, and mixtures thereof.

3. The hydrocarbon conversion process according to claim 1, wherein the inorganic support further comprises aluminum oxide, zirconium dioxide, titanium dioxide, zeolite, and mixtures thereof.

4. The hydrocarbon conversion process according to claim 1, wherein the tungsten of the second composition is in the form of tungsten oxide and the inorganic support comprises said silicon dioxide and said mixed magnesium-aluminum oxide, in a physical mixture with Y-zeolite.

5. The hydrocarbon conversion process according to claim 1, wherein the second composition contains 0.1 to 10 wt % of the doping agent based on the total weight of the second composition.

6. The hydrocarbon conversion process according to claim 1, wherein the first composition and the second composition are physically mixed.

7. The hydrocarbon conversion process according to claim 1, wherein the hydrocarbon feed stream comprises a paraffin selected from ethane, propane, butane, pentane, and mixtures thereof.

8. The hydrocarbon conversion process according to claim 1, wherein the hydrocarbon conversion process is carried out at a temperature in a range of 200–800° C.

9. The hydrocarbon conversion process according to claim 1, wherein the hydrocarbon conversion process is performed in a fixed bed of said hydrogen conversion catalyst.

10. The hydrocarbon conversion process according to claim 1, wherein the hydrocarbon conversion catalyst is pretreated by contacting the hydrocarbon conversion catalyst with an inert gas, an oxidizing gas, a reducing gas, or mixtures thereof, at a temperature in a range of 250° C. to 850° C. prior to contacting the hydrocarbon feed stream with the hydrocarbon conversion catalyst.

11. The hydrocarbon conversion process according to claim 1, wherein the hydrocarbon conversion process further comprises a regeneration step carried out by contacting a spent hydrocarbon conversion catalyst with an oxidizing gas at a temperature in a range of 200–700° C.

12. The hydrocarbon conversion process of claim 1, wherein the solid support of the first composition comprises a mixture of silicon dioxide and zirconium dioxide, and the inorganic support of the second composition further comprises Y-zeolite.

13. The hydrocarbon conversion process of claim 1, wherein the solid support of the first composition further comprises a mixed magnesium-aluminum oxide, and the inorganic support of the second composition further comprises Y-zeolite.

14. The hydrocarbon conversion process of claim 1, wherein the first composition and the second composition are present together in a single form as a physical mixture, wherein the single form is selected from an extrudate, a sphere, a pellet, and a tablet.

15. The hydrocarbon conversion process of claim 14, wherein the physical mixture comprises a powder of the first composition and a powder of the second composition.

16. The hydrocarbon conversion process of claim 1, wherein the hydrocarbon feed stream comprises propane and the hydrocarbon conversion process produces a product comprising ethylene and butene resulting from the conversion of propane, and further wherein a selectivity to total olefins, including the ethylene and butene, is at least about 80% by weight.

17. The hydrocarbon conversion process of claim 1, wherein the second composition comprises from 5 wt-% to 10 wt-% of said tungsten.

18. The hydrocarbon conversion process of claim 6, wherein the first composition and the second composition are physically mixed in weight ratio of 1:10 to 10:1.

19. The hydrocarbon conversion process of claim 18, wherein the first composition and the second composition are physically mixed in a weight ratio of 1:5 to 5:1.

\* \* \* \* \*